US011207151B2

United States Patent
He et al.

(10) Patent No.: US 11,207,151 B2
(45) Date of Patent: Dec. 28, 2021

(54) MARKER FOR USE IN THE LUNG OF PATIENTS

(71) Applicant: HANGZHOU BRONCUS MEDICAL CO., LTD., Hangzhou (CN)

(72) Inventors: Jie He, Shanghai (CN); Fei Sun, Shanghai (CN); Yongsheng Wang, Shanghai (CN); Shixin Liu, Shanghai (CN); Zhenjun Zi, Shanghai (CN)

(73) Assignee: HANGZHOU BRONCUS MEDICAL CO., LTD., Hangzhou (CN)

( * ) Notice: Subject to any disclaimer, the term of this patent is extended or adjusted under 35 U.S.C. 154(b) by 220 days.

(21) Appl. No.: 16/138,372

(22) Filed: Sep. 21, 2018

(65) Prior Publication Data

US 2019/0021810 A1 Jan. 24, 2019

Related U.S. Application Data

(63) Continuation of application No. PCT/CN2017/077423, filed on Mar. 21, 2017.

(51) Int. Cl.
*A61B 90/00* (2016.01)
*A61B 17/12* (2006.01)
*A61B 17/00* (2006.01)

(52) U.S. Cl.
CPC ........ *A61B 90/39* (2016.02); *A61B 17/12172* (2013.01); *A61B 2017/00809* (2013.01);
(Continued)

(58) Field of Classification Search
CPC .. A61B 90/39; A61B 2090/3904–3995; A61B 2017/00809; A61B 17/12172; A61B 2017/00867
See application file for complete search history.

(56) References Cited

U.S. PATENT DOCUMENTS 5,925,060 A * 7/1999 Forber ............. A61B 17/12022
606/191
6,090,125 A * 7/2000 Horton ............. A61B 17/12022
606/158

(Continued)

FOREIGN PATENT DOCUMENTS

| CN | 203815585 U | 9/2014 |
| JP | 2008-520359 A | 6/2008 |
| WO | WO 2014/146001 A2 | 9/2014 |

OTHER PUBLICATIONS

International Written Opinion of the International Search Authority dated Jun. 16, 2017, issued to International Application No. PCT/CN2017/077423.

(Continued)

*Primary Examiner* — Carrie R Dorna
(74) *Attorney, Agent, or Firm* — Stein IP LLC

(57) ABSTRACT

A marker for use in the lung of patients for marking the position of a lesion in the lung, wherein the marker comprises a self-expandable structure capable of self-expanding when released from a constricting device so as to implement marking function. Because the marker for use in the lung of a patient employs the self-expandable structure, when the position of a lesion is detected during a lung examination, the marker can be delivered to the position of the lesion via a catheter or a delivering device and substantively pressed and fixed by the lung when expanded at the lesion positions; as such, the lesion position can be located quickly by a surgeon during a surgery, the surgery time is shortened, the area of resection is reduced, and the post-surgery quality of life is improved for a patient.

6 Claims, 5 Drawing Sheets

(52) U.S. Cl.
CPC .............. *A61B 2017/00867* (2013.01); *A61B 2090/3912* (2016.02); *A61B 2090/3962* (2016.02)

(56) References Cited

U.S. PATENT DOCUMENTS

| | | | |
|---|---|---|---|
| 6,258,100 | B1 | 7/2001 | Alferness et al. ............ 606/108 |
| 2003/0050648 | A1 | 3/2003 | Alferness et al. ............ 606/108 |
| 2004/0073191 | A1* | 4/2004 | Soltesz ............ A61B 17/12159 604/516 |
| 2006/0135947 | A1 | 6/2006 | Soltesz et al. ................ 604/516 |
| 2007/0167980 | A1 | 7/2007 | Figulla et al. ................ 606/213 |
| 2007/0265656 | A1 | 11/2007 | Amplatz et al. .............. 606/200 |
| 2009/0082803 | A1 | 3/2009 | Adams et al. ................. 606/213 |
| 2010/0036241 | A1 | 2/2010 | Mayse et al. ................. 600/435 |
| 2012/0283768 | A1* | 11/2012 | Cox ................ A61B 17/12113 606/198 |
| 2012/0296160 | A1 | 11/2012 | Hill et al. ..................... 600/104 |
| 2014/0330309 | A1* | 11/2014 | Gonzalez ......... A61B 17/12104 606/213 |
| 2016/0354178 | A1* | 12/2016 | Mayes .................... A61B 5/05 |

OTHER PUBLICATIONS

International Search Report dated Jun. 16, 2017, issued to International Application No. PCT/CN2017/077423.

* cited by examiner

US 11,207,151 B2

MARKER FOR USE IN THE LUNG OF PATIENTS

CROSS-REFERENCE TO RELATED APPLICATIONS

This application is a bypass continuation application of International Application No. PCT/CN2017/077423, filed Mar. 21, 2017, which claims the benefit of priority to Chinese Application No. 201610167531.9, filed Mar. 23, 2016, in the State Intellectual Property Office, the disclosure of which is incorporated herein in their entireties by reference.

TECHNICAL FIELD

The present invention relates to the field of medical devices, in particular to a marker for use in the lung of patients.

BACKGROUND

With the progress of industrialization, environmental pollution, life stress, smoking and other unhealthy habits will significantly increase the incidence of lung disease, especially lung cancer. As the imaging technologies progress, such as the promotion of the use of low-dose spiral CT scans, more and more people without any symptoms have been diagnosed with early lung cancer or unidentified nodules. For these early lesions, radical surgery is the best treatment. However, early lesions are not only small in size, but also have densities very close to normal lung tissues, most lesion positions cannot be accurately detected during surgical operation. As such, the radical treatment of the lesion can only be ensured by extending the area of the resection. This surgical method may seriously reduce the quality of life of the patients after surgery and even reduce expected survival time of the patients after surgery. Therefore, a more effective and safe positioning method for nodules in the lung is desired in clinical practice.

SUMMARY

The objective of the present invention is to overcome the shortcomings of the prior art, providing a marker for used in the lung of the patients, which solves the problem of seriously reducing quality of life and the survival time of the patients after surgery existed in the traditional surgery which has to expand the area of the resection to ensure the radical treatment of the lesion.

The technical solution to achieve the above objective is as follows.

A marker for use in the lung of patients for marking a lesion cite in the lung according to the present invention comprises a self-expandable structure capable of self-expanding when released from a constricting device so as to implement marking function.

The marker for use in the lung of patients of the present invention employs a self-expandable structure, and it can be delivered to a lesion position via a constricting device (such as a general catheter or a dedicated delivery device) when a lesion is detected in a lung examination, and can be fixed in situ after being released and expanded at the lesion site, which can assist surgeons to accurately and quickly locate the lesion with fingers, shorten the surgery time, reduce the area of resection, improve the patient's post-surgery quality of life, and avoid the risk of reducing the patient's post-surgery life expectancy.

According to further development of the marker for use in the lung of patients of the present invention, the self-expandable structure is formed from a braided structure by a shape memory alloy.

According to further development of the marker for use in the lung of patients of the present invention, the self-expandable structure has a plano-convex lens shape.

According to further development of the marker for use in the lung of patients of the present invention, the self-expandable structure has a biconvex lens shape.

According to further development of the marker for use in the lung of patients of the present invention, the self-expandable structure is provided with a converged end at a distal end surface away from a releasing port of the constricting device.

According to further development of the marker for use in the lung of patients of the present invention, the self-expandable structure is provided with a converged end at a proximal surface adjacent to the releasing port of the constricting device.

According to further development of the marker for use in the lung of patients of the present invention, the self-expandable structure has spherical shape.

DESCRIPTION OF THE EMBODIMENTS

The invention will be further described with reference to the drawings and embodiments as follows.

The present invention provides a marker for use in the lung of patients for marking the position of lesions in the lung of patients, which facilitates the surgeons to quickly find or identify the position of the lesion during surgery. The marker for use in the lung of patients according to the present invention is an resilient self-expandable structure made of a shape memory alloy. Due to the resilience of the self-expandable structure, the marker can be constricted into an elongated profile, like a strip, by a constricting device such as a general catheter or a dedicated delivery device during delivery. It is then pushed out from the catheter after being delivered to the lung. Since the memory alloy is capable of returning to its original shape and the density of the lung tissue is extremely low, the self-expandable structure will be self-expanded to its original shape, and engaged in the lesion site, and thus achieve the function of marking. The structure of the marker for use in the lung of patients of the present invention will be described with reference to the accompanying drawings as follows.

Figure 1:
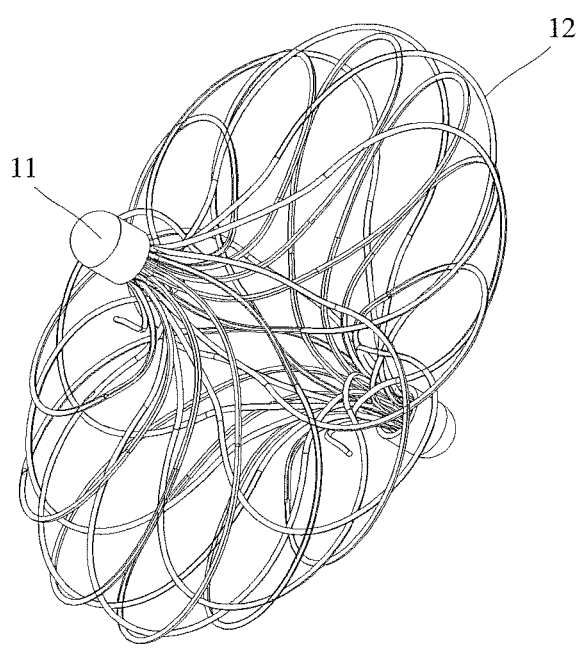
FIG. 1 is a top perspective view of a marker for use in the lung of patients according to a first embodiment of the present invention, with its self-expandable structure in an expanded state.

Referring to FIG. 1, it shows a schematic top perspective view of a marker for use in the lung of patients according to a first embodiment of the present invention, with its self-expandable structure in an expanded state.

As shown in FIG. 1, the marker for use in the lung of patients of the present invention is used to mark the positions of the lesions in the lung of patients, such as tumors, nodules, etc. The marker for use in the lung of patients comprises a self-expandable structure capable of self-expanding when being released from a constricting device so as to mark the lesion sites. The self-expandable structure 12 has a shape memory property, and is able to return to its original shape from a deformed state after and it has been released from the releasing port of the constricting device with the constriction force (i.e., the external force) is removed. In this way, the marker will be engaged at the lesion site and thus perform marking function.

Preferably, the self-expandable structure 12 is formed from a braided structure by a shape memory alloy, and the self-expandable structure 12 is mesh-shaped. The mesh-shaped self-expandable structure 12 exhibits a degree of deformation capacity, and can be deformed into a small profile when is restrained by a force for easily delivering. When the restrain force is removed, the mesh-shaped self-expandable structure 12 transforms into a large profile and is engaged in and fixed at the lesion site of the lung. The memory alloy may be a nickel-titanium memory alloy or a rubber material with resilience.

The self-expandable structure 12 has a biconvex lens shape. Alternatively, the self-expandable structure 12 may also has a plano-convex lens shape. The shape of the self-expandable structure 12 may also be spherical, cone, or the like.

Figure 3:
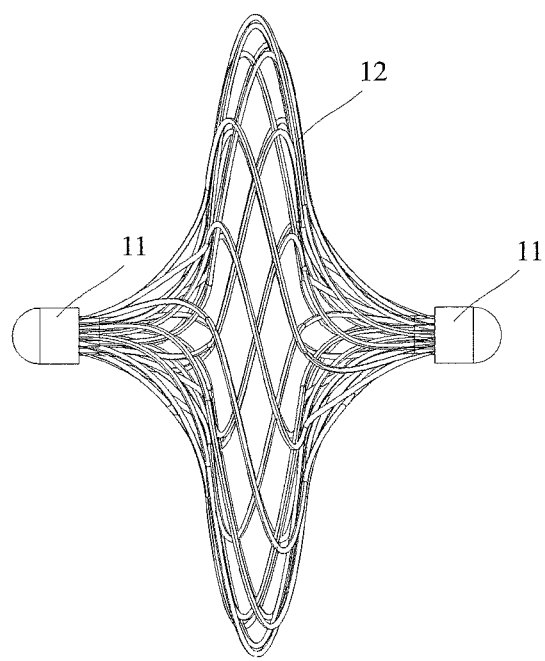
FIG. 3 is a side view of the marker for use in the lung of patients according to the first embodiment of the present invention, with its self-expandable structure in an expanded state.
Figure 4:
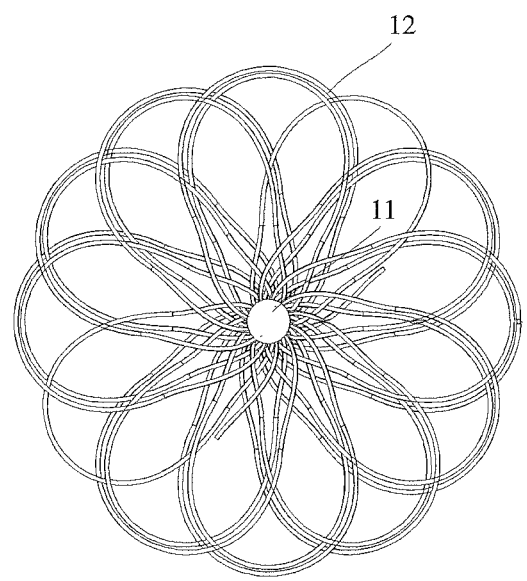
FIG. 4 is a top view of the marker for use in the lung of patients according to the first embodiment of the present invention, with its self-expandable structure in an expanded state.
Figure 5:
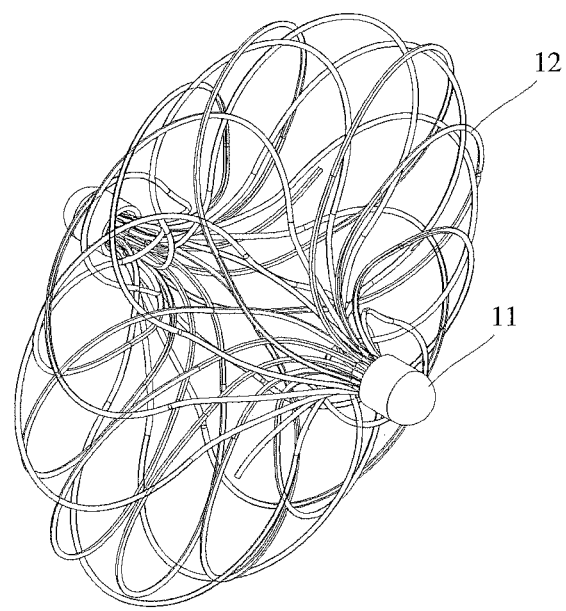
FIG. 5 is a bottom perspective view of the marker for use in the lung of patients according to the first embodiment of the present invention, with its self-expandable structure in an expanded state.

As shown in FIG. 3 to FIG. 5, according to the first embodiment, the self-expandable structure 12 presents a biconvex lens shape after expansion. The self-expandable structure 12 includes two converged ends 11, and the two converged ends 11 are arranged oppositely at two sides of the self-expandable structure 12. The converged ends 11 are cylindrical. The self-expandable structure 12 includes a proximal end surface adjacent to the releasing port of the constricting device and a distal end surface away from the releasing port of the constricting device. The proximal end surface and the distal end surface are oppositely disposed. Preferably, the two converged ends 11 are disposed at proximal surface and distal end surface, respectively.

Figure 2:
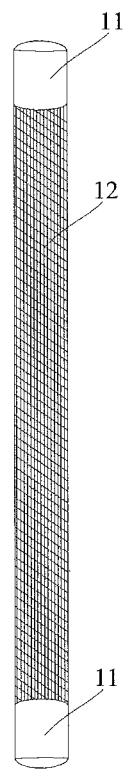
FIG. 2 is a schematic view of the marker for use in the lung of patients according to the first embodiment of the present invention, with its self-expandable structure in an collapsed state.

Referring to FIG. 2, it shows the self-expandable structure of the marker for use in the lung of patients according to the first embodiment of the present invention in a collapsed state before expansion, and the self-expandable structure of the marker for use in the lung of patients of the present invention will be described as follows with reference to FIG. 2.

As shown in FIG. 2, the self-expandable structure 12 is elongated before expansion, which can be conveniently delivered to the lesion site of the patient, and can be pushed to the lesion position via a general catheter or a dedicated delivery device. The self-expandable structure 12 is resilient.

The marker for use in the lung of patients is connected to the dedicated delivery device via the converged end 11 and is delivered to the lesion site of the lung of the patient by the dedicated delivery device, then the connection between the dedicated delivery device and the converged end 11 is released, so that the marker for use in the lung of patients is delivered to the lung. At the lesion site, the self-expandable structure 12 of the marker in the lung expands to its original shape after having been released from the delivery device, and is thus engaged in the lesion site in the lung, and functions as a marker.

Figure 6:
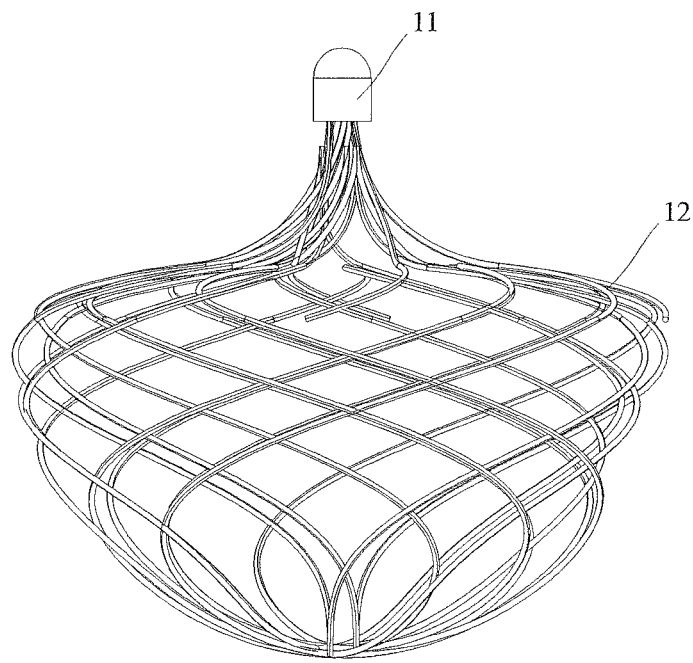
FIG. 6 is a schematic view of a marker for use in the lung of patients according to a second embodiment of the present invention, with its self-expandable structure in an expanded state.

Referring to FIG. 6, it shows a schematic view of a marker for use in the lung of patients according to a second embodiment of the present invention, with its self-expandable structure in an expanded state. The marker for use in the lung of patients according to the second embodiment of the present invention will be described as follows with reference to FIG. 6.

As shown in FIG. 6, according to the second embodiment, the structure of the marker for use in the lung of patients is different from that of the first embodiment in that the self-expandable structure 12 has a plano-convex lens shape after being expanded. The self-expandable structure 12 includes a single converged end 11, and the converged end 11 is disposed at a distal end surface of the releasing port away from the constricting device. The proximal end surface of the self-expandable structure 12 opposite to the distal end surface where the converged end 11 is located is planar. The self-expandable structure 12 is elongated in shape before expansion for easily delivering. The self-expandable structure 12 has a shape memory property and is able to return to its original state after having been released, so that when the marker for use in the lung of patients is delivered to the lesion site in the lung, the self-expandable structure 12 will automatically expands back to the plano-convex lens shape, and is engaged in the lesions site. It is convenient for the surgeon to find the lesion position of the patient by the marker for use in the lung of patients during the surgical operation, which facilitates the surgery.

Figure 7:
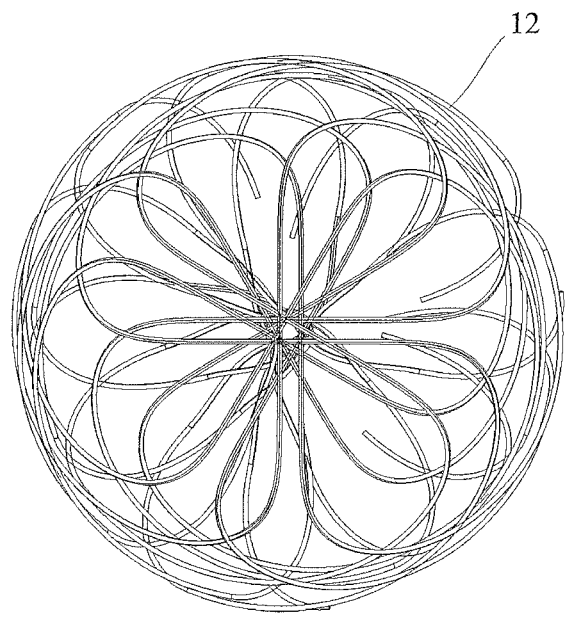
FIG. 7 is a schematic view of a marker for use in the lung of patients according to a third embodiment of the present invention, with its self-expandable structure in an expanded state.

As illustrated in FIG. 7, the marker for use in the lung of patients according to a third embodiment includes a spherical self-expandable structure 12, which is a mesh-like sphere in an expanded state.

The process of manufacturing and using the imarkers for use in the lung of patients of the present invention will be described as follows.

Taking nickel-titanium memory alloy as an example, the nickel-titanium memory alloy is braided into a mesh body, and is then shaped as an original shape, which may be a spherical shape, a plano-convex lens shape, a biconvex lens shape, a cone shape or other shape. After that, a self-expandable structure is formed, and then the end of the braided mesh body is converged to form a converged end or two converged ends, and thus the marker for used in the lung of patient is formed.

Figure 8:
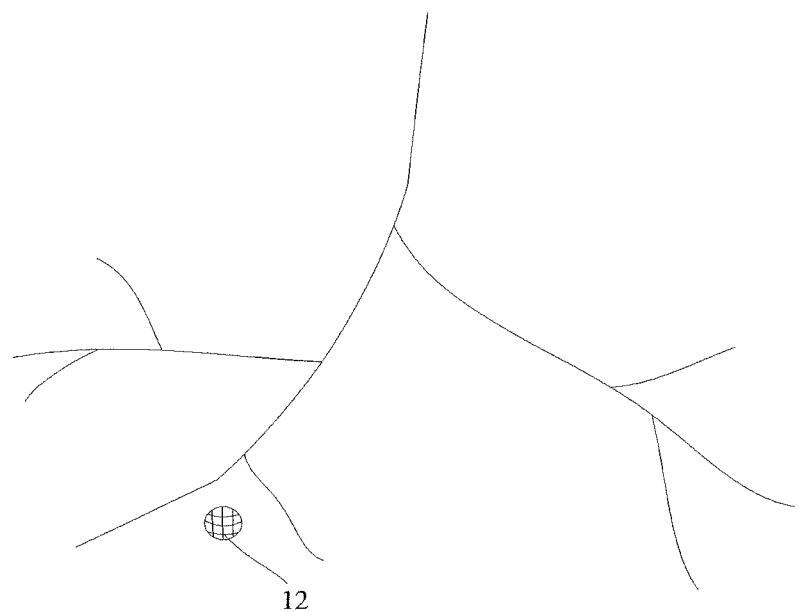
FIG. 8 shows the marker for use in the lung of patients according to the present invention in the lung for realizing marking function.

A dedicated delivery device may be used for delivery the marker for use in the lung of the patients. The marker for use in the lung of patients of the present invention can share a dedicated delivery device with an occlude device (which is used to block defect sites in the heart or blood vessels). The self-expandable structure is constricted into elongated shape upon loading, then placed in the delivery device, and kept in the elongated shape due to the constraint of the delivery device. The dedicated delivery device is delivered to the lesion site in the lung of the patient, and then the marker is pushed out from the sheath through an internal structure of the delivery device, and the self-expandable structure is engaged at or near the position of lesion in the lung, thus functioning as a marker. Referring to FIG. 8, it shows the marker at the position of a lesion site which can perform marking function. During the surgery, the surgeon can use his/her fingers to touch the outer surface of the lung, and identify the position of the foreign matter of the lung tissue by feelings of pressure changes on the finger, thereby rapidly locating the lesion site and determining the minimum area of resection. In this way, the operation time, and thus the recovery time of the patient is shortened, and quality of life of the patient after surgery is also significantly improved.

The present invention has been described in detail above with reference to the embodiments and drawings, and various modifications of the present invention can be made by those skilled in the art in light of the above description. Therefore, some of the details of the embodiments are not to be construed as limiting the invention, the scope of the invention is defined by the appended claims.

What is claimed is:

1. A method for marking a position of a lesion in the lung of a patient, comprising:
    loading a marker into a delivery device:
        wherein the marker comprises:
            a self-expandable structure having a longitudinal axis, and first and second ends that are opposite to each other along the longitudinal axis, the self-expandable structure being movable between a compressed configuration when received in the delivery device and an expanded configuration when released from the delivery device, wherein the self-expandable structure in the expanded configuration defines a plurality of passages passing through the self-expandable structure along the longitudinal axis and communicating with outside of the marker for gas flowing through; and
            first and second converged elements respectively connected with the first and second ends of the self-expandable structure, wherein each of the first and second converged elements comprises an opening end facing towards the self-expandable structure and receiving the respective end of the self-expandable structure and a closed end facing away from the self-expandable structure, wherein the opening end and the closed end are opposite to each other along the longitudinal axis;
    delivering the marker to the position of the lesion in the lung of the patient by means of the delivery device,
    releasing the marker from the delivery device to the position of the lesion in the lung of the patient so that the self-expandable structure of the marker self-expands to become the expanded configuration so as to mark the position of the lesion in the lung of the patient, and
    identifying the position of the marker in the lung tissue by feelings of pressure changes on a finger touching the human body surface of the patient corresponding to the lung, thereby rapidly locating the position of the lesion.

2. The method according to claim 1,
    wherein the delivery device comprises:
    a sheath for receiving the marker, and
    an internal structure for pushing the marker out of the sheath, and
        wherein the step of releasing the marker comprises:
    pushing the marker out of the sheath by means of the internal structure so as to release the marker from the delivery device.

3. The method according to claim 1,
    wherein the step of loading the marker into the delivery device comprises:
    connecting the first and second converged elements of the marker with the delivery device so as to load the marker into the delivery device; and
        wherein the step of releasing the marker further comprises:
        releasing the connection between the first and second converged elements of the marker and the delivery device so as to release the marker from the delivery device.

4. The method according to claim 1, wherein the self-expandable structure of the marker in the expanded configuration released from the delivery device has a biconvex lens shape.

5. The method according to claim 1, wherein the lesion in the lung of the patient is a tumor or a nodule.

6. The method according to claim 1, wherein the method further comprises withdrawing the delivery device out of the lung of the patient.

* * * * *